(12) United States Patent
Galeev et al.

(10) Patent No.: US 11,076,766 B2
(45) Date of Patent: Aug. 3, 2021

(54) SYSTEMS AND METHODS FOR PROVIDING USER INSIGHTS BASED ON HEART RATE VARIABILITY

(71) Applicant: BEIJING SHUNYUAN KAIHUA TECHNOLOGY LIMITED, Beijing (CN)

(72) Inventors: Artem Galeev, Vancouver (CA); Yan Vule, Vancouver (CA)

(73) Assignee: BEIJING SHUNYUAN KAIHUA TECHNOLOGY LIMITED, Beijing (CN)

(*) Notice: Subject to any disclaimer, the term of this patent is extended or adjusted under 35 U.S.C. 154(b) by 562 days.

(21) Appl. No.: 15/956,132

(22) Filed: Apr. 18, 2018

(65) Prior Publication Data

US 2018/0303356 A1    Oct. 25, 2018

Related U.S. Application Data

(60) Provisional application No. 62/487,333, filed on Apr. 19, 2017.

(51) Int. Cl.
| | |
|---|---|
| *A61B 5/024* | (2006.01) |
| *A61B 5/00* | (2006.01) |
| *A61B 5/0205* | (2006.01) |
| *A61B 5/1455* | (2006.01) |
| *A61B 5/11* | (2006.01) |
| *A61B 5/145* | (2006.01) |

(52) U.S. Cl.
CPC ........ *A61B 5/02405* (2013.01); *A61B 5/4035* (2013.01); *A61B 5/0082* (2013.01); *A61B 5/0205* (2013.01); *A61B 5/02438* (2013.01); *A61B 5/1118* (2013.01); *A61B 5/1455* (2013.01); *A61B 5/14532* (2013.01); *A61B 5/681* (2013.01); *A61B 5/7207* (2013.01)

(58) Field of Classification Search
CPC ..... A61B 5/00; A61B 5/0205; A61B 5/02438; A61B 5/1118; A61B 5/1455; A61B 5/0082; A61B 5/7207; A61B 5/14532; A61B 5/681
See application file for complete search history.

(56) References Cited

U.S. PATENT DOCUMENTS

| | | | |
|---|---|---|---|
| 2010/0274308 A1* | 10/2010 | Scott ................. | A61N 1/36135 607/9 |
| 2017/0172520 A1* | 6/2017 | Kannan ............... | A61B 5/7282 |
| 2017/0369075 A1* | 12/2017 | Hwang ................ | B60W 40/08 |
| 2018/0056131 A1* | 3/2018 | Nakazawa ......... | A63B 71/0616 |

* cited by examiner

*Primary Examiner* — Eric J Messersmith
(74) *Attorney, Agent, or Firm* — Young Basile Hanlon & MacFarlane, P.C.

(57) ABSTRACT

A system can include a wearable device that obtains real-time physiological data and activity data from a user and transmits that data to another device. A computing device can receive HRV and activity data and determine whether the user's autonomic nervous system is in a predominantly sympathetic or parasympathetic state. For example, the determination can include comparing an average variance in a portion of the HRV data with a threshold value. In response to determining that the user's autonomic nervous system is in a sympathetic state, the device can perform an action.

20 Claims, 9 Drawing Sheets

SYSTEMS AND METHODS FOR PROVIDING USER INSIGHTS BASED ON HEART RATE VARIABILITY

PRIORITY CLAIM

This application claims priority to U.S. Provisional Patent Application No. 62/487,333, entitled "SYSTEMS AND METHODS FOR PROVIDING USER INSIGHTS BASED ON HEART RATE VARIABILITY" and filed Apr. 19, 2017, which is hereby incorporated herein in its entirety.

FIELD OF THE DISCLOSURE

This disclosure relates generally to systems and methods that use non-invasive electro-optical technology for sensing, measuring, and interpreting physiological parameters relating to a user's heart rate, and more specifically, to systems and methods for providing user insights or taking actions based on a user's heart rate variability.

BACKGROUND

Many portable devices have been developed in which optical sensors are used to detect variation in blood flow through arteries or blood volume in subcutaneous tissue. Applications include the monitoring of heart rate, glucose level, apnea, respiratory stress, and other physiological conditions. The optical sensors often comprise one or more light sources that illuminate a targeted portion of the human body and one or more associated optical detectors that receive a portion of the optical energy emitted by the light sources.

One area of growing interest in the use of physiological monitors is with respect to personal wellness and/or physical exercise for purposes of fitness training, weight loss, or monitoring general health. Technological advances relating to optical sensors, signal processing, and display devices have made it possible to realize small, light-weight physiological monitors that can be embodied as devices that may be comfortably worn by a user. Such wearable devices may include, for example, wrist watches, bracelets, and arm bands.

Heart rate variability ("HRV") is a physiological phenomenon of fluctuations of time intervals between heartbeats. HRV can provide indications about the overall physical health of a person, including whether the person's body, such as their nervous system, is stressed or relaxed. HRV can also provide a baseline score against which fluctuations are compared, to determine whether a person's body is undergoing a healthy (or unhealthy) amount of physical activity.

The human autonomic nervous system is a part of the peripheral nervous system that supplies smooth muscle and glands, influencing the function of internal organs such as the heart, stomach, and intestines. This system functions primarily unconsciously. The autonomic nervous system includes two subparts: the sympathetic nervous system and the parasympathetic nervous system. The sympathetic nervous system is considered the "fight-or-flight" system while the parasympathetic nervous system is considered the "rest and digest" system. The two systems have opposite actions in that one activates a physiological response while the other inhibits it. By determining the state of a person's autonomic nervous system, it is possible to infer information about the user's overall state of physiologic stress. For example, if a person's nervous system is in a sympathetic state during a period when the body should be relaxed, it can indicate stress or a lack of physiologic well-being.

Applicant has found that, using HRV, it is possible to determine whether a person's body is in a predominantly sympathetic or parasympathetic state. This information can be used to inform the user more accurately about their physiologic state and provide actionable information or recommendations to the user for improving their health.

SUMMARY OF THE DISCLOSURE

The system can continuously test physiological parameters of a user, including periodic recording of heart rate variability, to assess stress level and physical fitness of users. The assessment may be carried out automatically during user's usual daily physical activity. Based on the assessment, various actions can be taken.

The system may accomplish the assessment by using a wearable device such as a bracelet, watch, arm band, chest strap, or any other wearable device, to collect data from different sensors (movements, time, illumination, atmosphere pressure and any others). Based on the sensor data, a processor in the system (on the wrist-word device or on a server) can identify patterns of user's activity, such as sitting, walking, jogging, driving, television watching and others. The wrist-worn device and/or server may look for the known patterns in real time. If a pattern appears and is recognized, the wrist-worn device may switch on HRV recording. A server may compare HRV data of the same patterns over time and recognize declining or improving stress level and physical fitness levels in the individual. Although the user's activity can be taken into account when interpreting physiological data, heart rate variability can also be determined without regard to the user's activity.

In one embodiment, the system includes a wearable device that obtains real-time physiological data and activity data from a user and transmits that data to another device. For example, the wearable device can transmit the data to a computing device such as a cell phone, laptop computer, desktop computer, tablet, a remote server, or a combination thereof. A computing device having a processor can perform various stages for interpreting the physiological data and activity data.

For example, the processor can first receive the physiological data and the activity data. It can then calculate a first HRV score for the user based on physiological data from first time period, such as an average HRV score for the previous week. The processor can also calculate a second HRV score for the user based physiological data from a second time period, such as a moving average HRV score for the last seven days. Other time periods can be used as well, such as the previous day, week, or month.

The processor can present the user with at least one of the first and second HRV scores. In some examples, the user is presented with a score based on the first and/or second HRV scores but is different from the HRV scores. In other examples, the user is presented with the first and second HRV scores, as well as additional HRV scores based on additional periods of time. The score can be provided on a graphical user interface ("GUI") of the wearable device or another device, such as the user's phone. In one example, a graphical display is provided on a GUI that includes indicators for each day of the week. In response to a user selecting an indicator for a day of the week, the GUI can display an HRV score for that selected day, including a trailing 7-day average score for that day.

The processor can perform further calculations on the HRV scores, such as calculating a magnitude of a change in HRV scores between the first HRV score and second HRV score. The processor can compare the calculated change to a threshold value, and if the calculated change is larger than the threshold value, take an action in response.

Taking an action in response can include a variety of different actions. In one example, the action is providing an alert to the user, such as by sending a notification to the user's phone or wearable device. In another example, the action includes suggesting an action or activity for the user to engage in. This can include suggesting a specific type of exercise for the user to undertake.

In another example, a system is provided that includes a wearable device that obtains real-time physiological data, including HRV data, from a user, obtains activity data from a user, and transmits the real-time physiological data and activity data. A computing device having a processor can perform various stages for interpreting the physiological data and activity data.

The computing device can receive the HRV and activity data and determine, based on at least the HRV data and activity data, whether the user's autonomic nervous system is in a predominantly sympathetic or parasympathetic state. For example, the determination can include comparing an average variance in a portion of the HRV data with a threshold value. The threshold value can be, for example, 5 seconds, 10 seconds, or any other value. In response to determining that the user's autonomic nervous system is in a sympathetic state, the device can perform an action.

Performing an action can include a variety of different actions. For example, it can include providing an alert to the user indicating that the user is under stress, recommending an activity for the user to perform, dimming or turning off a light, or playing or adjusting the volume of music.

The above and further objects, features and advantages thereof will be recognized by those skilled in the pertinent art from the following detailed description of the invention when taken in conjunction with the accompanying drawings. It is to be understood that both the foregoing general description and the following detailed description are illustrative and explanatory only and are not restrictive of the claims.

The accompanying drawings, which are incorporated in and constitute a part of this specification, illustrate several embodiments and together with the description, serve to explain the principles of the disclosure.

DESCRIPTION OF THE EMBODIMENTS

Figure 1:
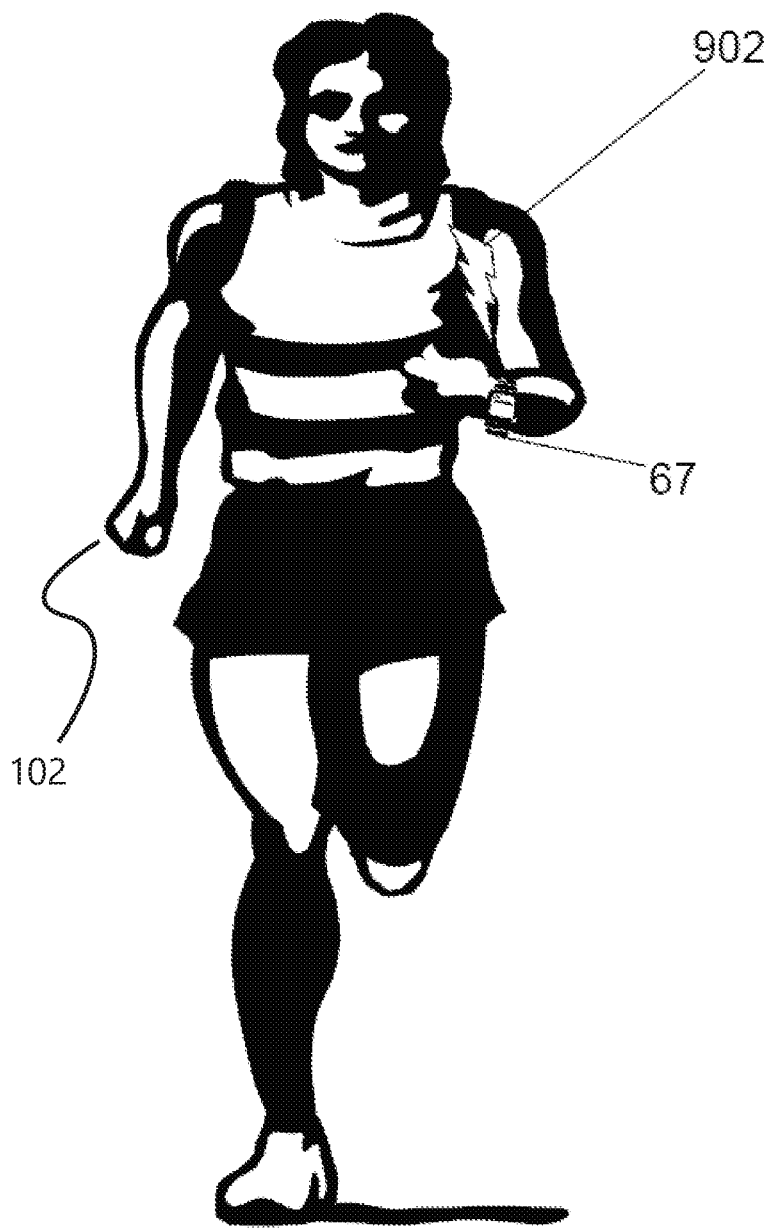
FIG. 1 is an example image of a jogger wearing a device for obtaining and transmitting real-time physiological data in accordance with an embodiment.

Disclosed herein are embodiments of an apparatus for sensing, measuring, and displaying physiological information. In one embodiment, the system may continuously test physiological parameters of a user, including periodic recording of HRV, to assess stress level and physical fitness of users. The assessment may be carried out automatically during user's usual daily physical activity.

The system may accomplish the assessment by using a wearable device such as a bracelet, watch, arm band, chest strap, or any other wearable device to collect data from various sensors. The sensor data can include both physiological data (such as heart rate or blood oxygen level, for example) and activity data (such as accelerometer-based movements, time, illumination, atmospheric pressure, and any others). Based on the sensor data, a processor in the system (either on the wearable device, a paired computing device, or a remote server) can identify patterns of user's activity, such as sitting, walking, jogging, driving, television watching and others. The processor can then calculate HRV by taking into account the user's activity when parsing the physiological data.

In one example, the wearable device may include one or more optical sensors incorporated into the device. The optical sensor(s) may be incorporated at a location of the wearable device such that, in use, a surface of the optical sensor may be adjacent or in close proximity to a targeted area of a user's body. In one embodiment, the optical sensor(s) may comprise one or more light sources for emitting light proximate the targeted area and one or more optical detectors for detecting reflected light from the targeted area.

In one embodiment, the physiological information may be heart rate information. In other embodiments, the physiological information may be blood pressure information. Alternatively, the physiological information may be any information associated with a physiological parameter derived from information received by the wearable device. Regardless, the physiological information may be used in the context of, for example, athletic training, physical rehabilitation, patient monitoring, and/or general wellness monitoring. Of course, these examples are only illustrative of the possibilities and the device described herein may be used in any suitable context.

While some of the example systems and devices described herein may be depicted as wrist-worn devices, one skilled in the art will appreciate that the systems and methods described below can be implemented in other contexts, including the sensing, measuring, and display of physiological data gathered from a device worn at any suitable portion of a user's body, including but not limited to, other portions of the arm, other extremities, the head, and/or the chest.

The wearable device, or any number of additional devices, can be used to collect physiological data from an individual. One such device is a pulse oximetry device. Pulse oximetry is used to determine the oxygen saturation of arterial blood. Pulse oximeter devices typically contain two light emitting diodes: one in the red band of light (660 nanometers) and one in the infrared band of light (940 nanometers). Oxyhemoglobin absorbs infrared light while deoxyhemoglobin absorbs visible red light. Pulse oximeter devices also contain sensors that detect the ratio of red/ infrared absorption several hundred times per second. A preferred algorithm for calculating the absorption is derived from the Beer-Lambert Law, which determines the transmitted light from the incident light multiplied by the exponential of the negative of the product of the distance through the medium, the concentration of the solute and the extinction coefficient of the solute.

Reference will now be made in detail to certain illustrative embodiments, examples of which are illustrated in the accompanying drawings. Wherever possible, the same reference numbers will be used throughout the drawings to refer to the same or like items.

FIG. 1 illustrates a runner 102 wearing a physiological monitoring device 67 which obtains real-time physiological data for the runner, and processes stores that data on the device 67 or a separate device. The data can then be sent via transmission 902 over a network to a web portal for analysis in an embodiment. The runner subsequently receives a communication based on the analyzed physiological data in the form of an advertisement or personalized content.

Figure 2:
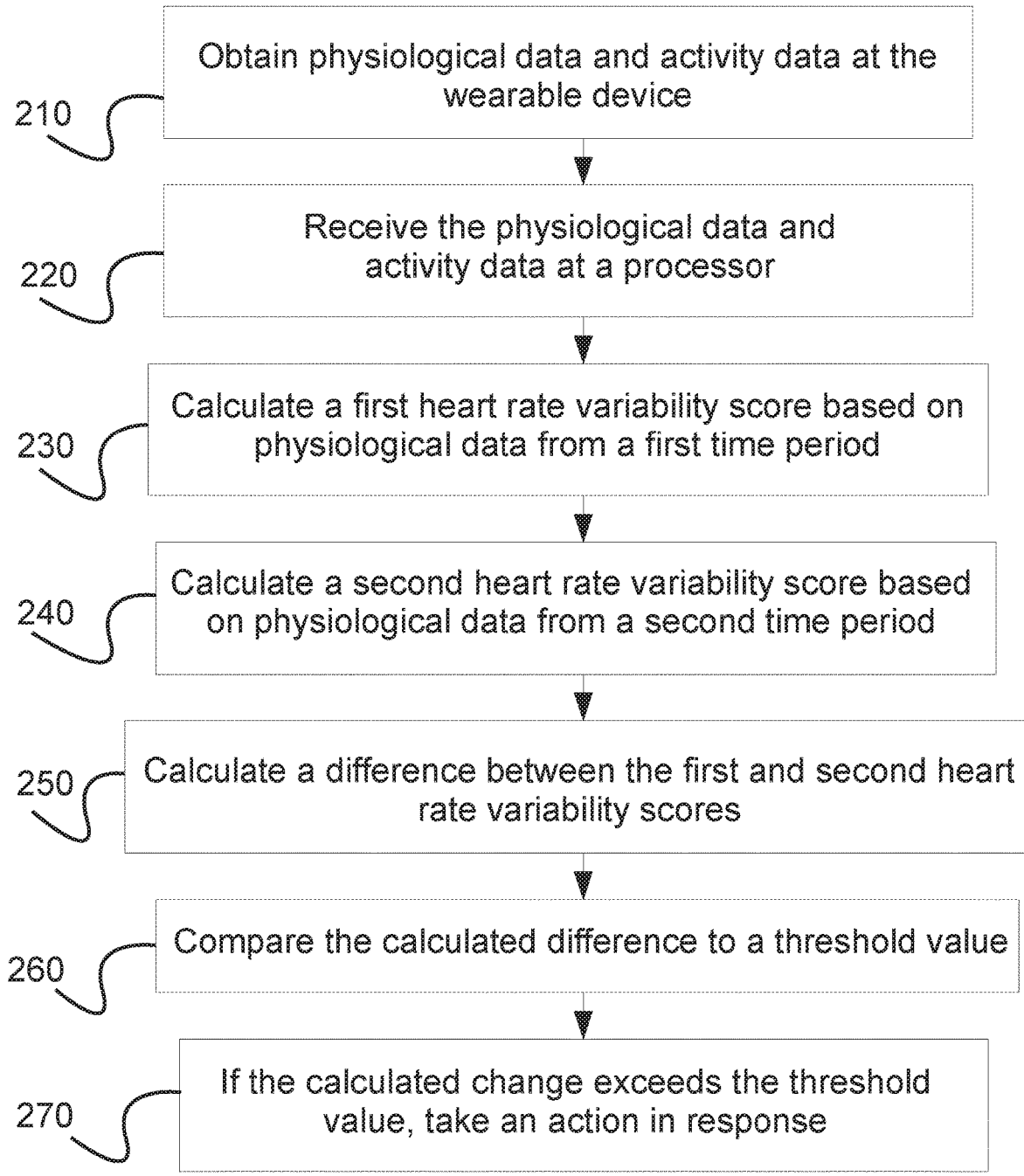
FIG. 2 is an exemplary flow chart in accordance with an embodiment.

FIG. 2 is an example flow chart of a method utilized in one embodiment. Step 210 can include obtaining physiological data and activity data at the wearable device 67. Several different devices may be used to obtain physiological data. For example, to obtain heart rate, pulse oximeters, pseudo-pulse oximeters, EKG devices, and other known devices may be used. Dickinson, U.S. Pat. No. 6,675,041, for an Electronic Apparatus And Method For Monitoring Net Calorie Intake, discloses such a device and is hereby incorporated by reference in its entirety. Exemplary methods of obtaining physiological data useful with the present invention are disclosed in U.S. Patent Publication Number 2005/0251056, U.S. Patent Publication Number 2005/0251055, U.S. Patent Publication Number 2005/0251054, U.S. Patent Publication Number 2005/0251057, U.S. Patent Publication Number 2005/0251051, U.S. Patent Publication Number 2005/0251424, all of which are hereby incorporated by reference in their entireties.

Similar devices can be used to obtain activity data. Activity data can include accelerometer-based movement information, GPS-based location information, time and duration, illumination, atmospheric pressure, temperature, step information, running speed and distance, and any other data describing the physical state of the user, the wearable device 67, or the environment.

In one example, the physiological and activity data are obtained and stored in a memory store of the wearable device 67 and later uploaded to a computing device such as a phone, tablet, laptop or desktop computer, or a remote server. In another example, the physiological and activity data are obtained and immediately transmitted to the computing device.

At step 220 a processor of the computing device receives the physiological data and activity data from the wearable device 67. The data can be obtained via any type of electronic communication, such as wireless transmission according to a wireless protocol such as WIFI or BLUETOOTH.

Having received the physiological data and activity data, at step 230 the processor can calculate a first HRV score based on physiological data from a first time period. For example, the processor can calculate an HRV score based on an hour-long period of time when the user is in a resting state. In another example, the first HRV score can be an average score based on multiple time periods and/or multiple days. For example, the first HRV score can be based on the previous week.

The wearable device 67 can sample across discrete periods of time, such as 120 seconds. Any other period of time can also be used. In some examples, the wearable device 67 only samples during periods of time when the user is in a resting state. In other examples, the wearable device 67 samples during a period of time that is later correlated to an activity that the user was engaged in at the time. The user's activity can be determined by, for example, processing the real-time activity data of the user. For example, if the user's heartbeat is near their average resting heartbeat and the accelerometer on the wearable device indicates that the user is not walking, the processor can determine that the user is stationary. Additional methods for interpreting the activity data are discussed with respect to FIGS. 8 and 9.

An HRV score can be calculated by measuring the beat-to-beat intervals of a user's heartbeat and performing further calculations based on those intervals. For example, the additional calculations can include a root mean square of successive differences, or RMSSD, which is the square root of the mean of the squares of the successive differences between adjacent beat-to-beat intervals of the user's heartbeat. In one example, an HRV score is calculated using the following equation:

$$R=(Ln(RMSSD)-2)*33.3 \tag{1}$$

Where R is the result, or HRV score and RMSSD is the square root of the mean of the squares of the successive differences between adjacent beat-to-beat intervals of the user's heartbeat, where RMSSD is collected during a period of time such as a 24-period.

In some examples, an HRV score can be based on Equation 1, provided above, and then weighted based on the user's age. A K index can be provided for each age and can be used to weight the HRV score appropriately based on the user's age. For example, a 55-year-old user can be associated with a K index of about 1.85. To calculate the weighted HRV score, the result from Equation 1 would be multiplied by 1.85. Throughout the discussion of this disclosure, the term "HRV score" is meant to encompass an HRV score obtained by (1) using Equation 1, (2) using Equation 1 with a K index for weighting, (3) using another equation based on RMSSD, or (4) using any other equation that takes into account the successive differences between adjacent beat-to-beat intervals of the user's heartbeat.

At step 240 the processor of the computing device can calculate a second HRV score based on physiological data from a second time period. For example, the second HRV score can be a moving average score based on the previous seven days. The second HRV can also be an HRV score for a single day. Any other time periods can be used, such as by calculating a moving average for the previous two, three, four, five, or six days, for example.

At step 250, the processor of the computing device can calculate a magnitude of a difference between the first and second HRV scores. For example, for a first HRV score of 65 and a second HRV score of 61, the difference would be four. Similarly, for a first HRV score of 44 and a second HRV score of 54, the difference would be 10.

At step 260, the processor of the computing device can compare the calculated difference to a threshold value. In one example, the threshold value is 5. Any other value can be chosen for the threshold value, but Applicant has determined that a change of at least 5 points can indicate a significant shift.

In some examples, this step can also include comparing one or more HRV scores directly to a threshold number. For example, a third HRV score can be calculated based on a recent time period, such as the previous 24 hours. The third HRV score can be compared to one or more threshold numbers. For example, if the HRV scores are provided on a scale of 0-100, then a lower threshold of 20 and an upper threshold of 80 can be used. If the third HRV score falls below the lower threshold or above the upper threshold, the system can take further action in accordance with the remaining steps discussed below. The comparison of the HRV score to upper and lower thresholds can also be done for the first and second HRV scores described above.

At step 270, if the processor determines that the calculated change between the first and second HRV scores exceeds the threshold value, it can take an action in response. Any type of action can be taken. For example, taking an action can include displaying a graphic on a GUI associated with the computing device, the wearable device 67, or any other device associated with the user. Taking an action can also include updating or altering the graphic on a GUI, such as by applying a particular color to a portion of the graphic or by updating the number or numbers displayed by the graphic. For example, if the calculated difference exceeds a threshold in a manner indicating an improvement in the user's health, a green-colored graphic can be displayed. Similarly, if the difference exceeds a threshold in a manner indicating a decline in the user's health, a red color can be displayed on the GUI. An example GUI is described in more detail with respect to FIG. 5.

In addition to displaying information, other actions can be taken as a result of the calculated difference between the first and second HRV scores being above a threshold. For example, if the HRV scores indicate that the user's health has declined since the previous week, the system can provide the user with an alert. The alert can include an informational notice presented to the user on a display of the wearable device 67 or an associated computing device. The alert can inform the user of the reason why their health has declined. For example, if the user's HRV score has dropped too low or risen too high, the system can provide an alert informing the user of this fact. The alert can also include information regarding possible causes of the undesirable HRV score, as well as proposing various methods for improving the HRV score. The alert can also includes sounds, vibrations, or any other function available to the wearable device 67 or computing device of the user.

In an example where the user is provided with a recommended action to take to improve their HRV score, the recommendation can encompass any feasible action, activity, or lack thereof. For example, if an HRV score indicates that the user's body has undergone an excessive amount of exercise-related physical stress, the recommendation can be to cease all strenuous exercise for a period of time, such as 12 hours, 24 hours, or 48 hours. Similarly, the user's wearable device 67 or computing device can inform the user that additional physical activity would benefit the user. The system can suggest, for example, that the user go for a run or walk later that day.

In some examples, a user's mobile device can take various actions to assist the user in remedying an HRV score that is too low or too high. For example, a mobile device can determine that the user is listening to music and decrease the volume of the music to reduce stress. In another example, the mobile device can be paired to a wirelessly controlled light fixture or set of fixtures, and can decrease the brightness of the lights in order to reduce stress. In yet another example, the mobile device can determine that the user is driving based on GPS locations and suggest a convenient location for the user to stop and either rest or perform an exercise. In another example, the system can recommend alterations to the user's sleep habits, such as going to bed earlier or waking up later.

Figure 3:
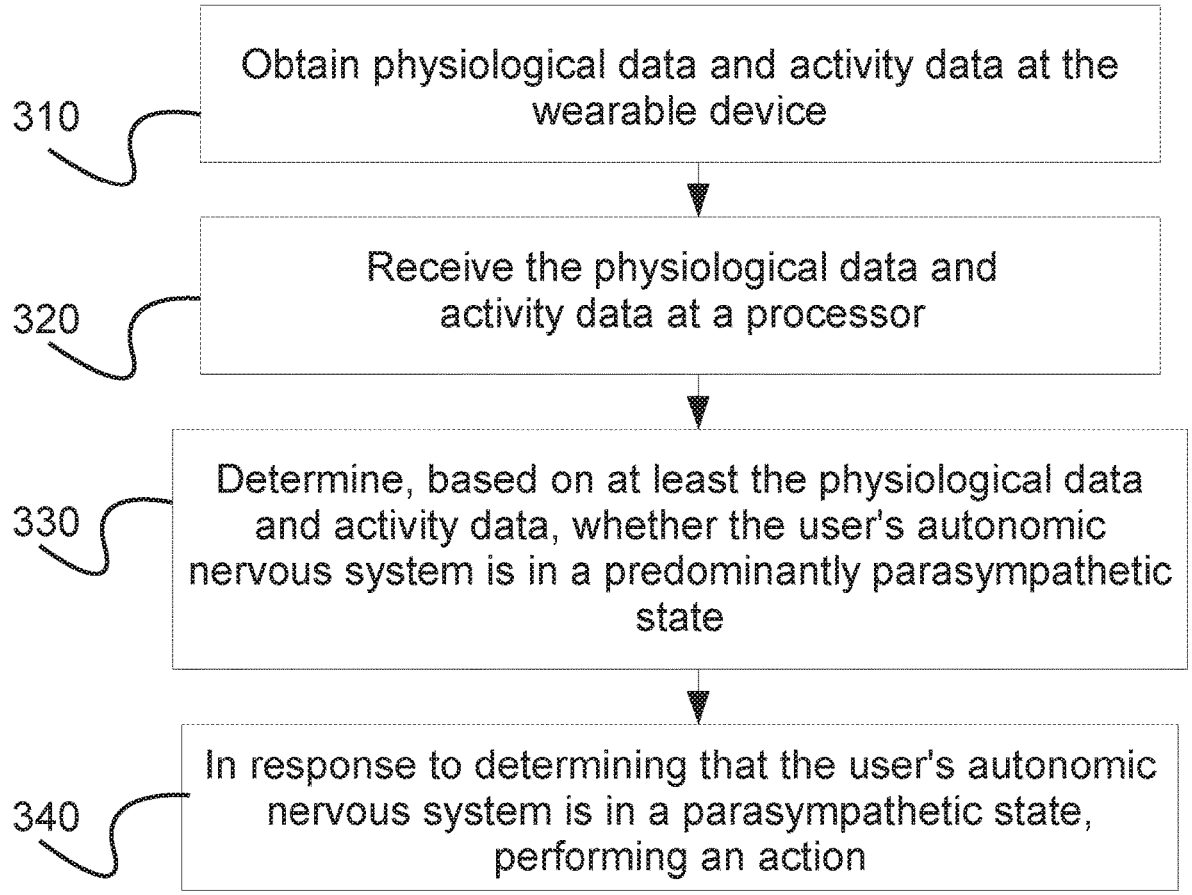
FIG. 3 is an exemplary flow chart in accordance with an embodiment.

An additional exemplary flow chart in accordance with another embodiment is illustrated in FIG. 3. Stage 310 can include obtaining physiological data and activity data at the wearable device 67. In one example, the physiological and activity data is obtained and stored in a memory store of the wearable device 67 and later uploaded to a computing device such as a phone, tablet, laptop or desktop computer, or a remote server. In another example, the physiological and activity data is obtained and immediately transmitted to the computing device.

Stage 320 can include receiving the physiological data and activity data at a processor. For example, a processor of the computing device receives the physiological data and activity data from the wearable device 67. The data can be obtained via any type of electronic communication, such as wireless transmission according to a wireless protocol such as WIFI or BLUETOOTH.

Stage 330 can include determining, based on at least the physiological data and activity data, whether the user's autonomic nervous system is in a predominantly sympathetic or parasympathetic state. This can be done by, for example, comparing an HRV score for the user against one or more thresholds. In one example, multiple thresholds are used to define categories associated with a general health assessment.

The categories for a healthy adult can be, for example: 0-19 (very poor); 20-39 (poor), 40-59 (good), 60-79 (high), and 80-100 (caution required). For children, the categories can be shifted up by about 20 points. For elderly adults, the categories can be shifted down by about 20 points. An HRV score that is too high indicates excessive parasympathetic nervous system activity, indicating that the user's body is undergoing stress.

The system can determine that a user's autonomic nervous system is in a predominantly parasympathetic state if the HRV score falls into a particular category or rises above a threshold. In one example, the system identifies a predominantly parasympathetic state when the user's HRV score is in the "caution required" category explained above. For an adult, this category can correspond to a score above 80. In another example, the system identifies a predominantly parasympathetic state when the user's HRV score is above a particular threshold, such as 70. Similarly, the system can identify that a user's nervous system is in a predominantly sympathetic state when the user's HRV score is in the "very poor" or "poor" categories, or when the HRV score is below a particular threshold number, such as 30.

In some examples, the system can determine whether the user's autonomic nervous system is in a predominantly parasympathetic state by comparing a weighted HRV score to one or more thresholds. The weighted HRV score can be calculated by first calculating an HRV score and then multiplying it by a weighting factor. The weighting factor can take into account any relevant information, such as the user's age, sex, physical fitness level, and fitness history. For example, if the user is a child the weighting factor can be 0.8. In that example, an HRV score of 70 would result in a weighted HRV score of 56. Similarly, for an older user, the weighting factor can be 1.2. In that example, an HRV score of 70 would result in a weighted HRV score of 84. Any other weighting factors can be used based on any relevant criteria.

If the user's HRV score falls into a particular category or surpasses a threshold indicating that the user's autonomic nervous system is in a parasympathetic state, at stage 340, in response to that determination the system can perform an action. Performing an action can include, for example, providing an alert to the user indicating that the user is under stress. For example, an information alert can be displayed on the user's wearable device 67 or a mobile device paired to the wearable device 67. The alert can be accompanied by sound and/or vibration in one example.

The alert can include information to help the user determine how and why their body is under stress. For example, the alert can include a text explanation that the user's heartbeat signature indicates that they are experience stress. The alert can include an information button that, if selected by the user, provides a more detailed explanation of HRV, including how it is calculated and what it means. The alert can also include recommendations for the user, such as resting or performing a particular activity.

In addition to, or instead of, providing an alert, the system can perform an action intended to help the user recover from their parasympathetic state. For example, the system can recommend an activity for the user to perform. The activity can include resting or refraining from any strenuous physical activity, in one example. In another example the activity can include standing up, walking, running, or performing any other physical activity or exercise. In yet another example, the activity can include dimming or turning off a light, adjusting the volume of music or of a television, adjusting the temperature, or taking any other action that can influence the user's physical stress levels.

Figure 4:
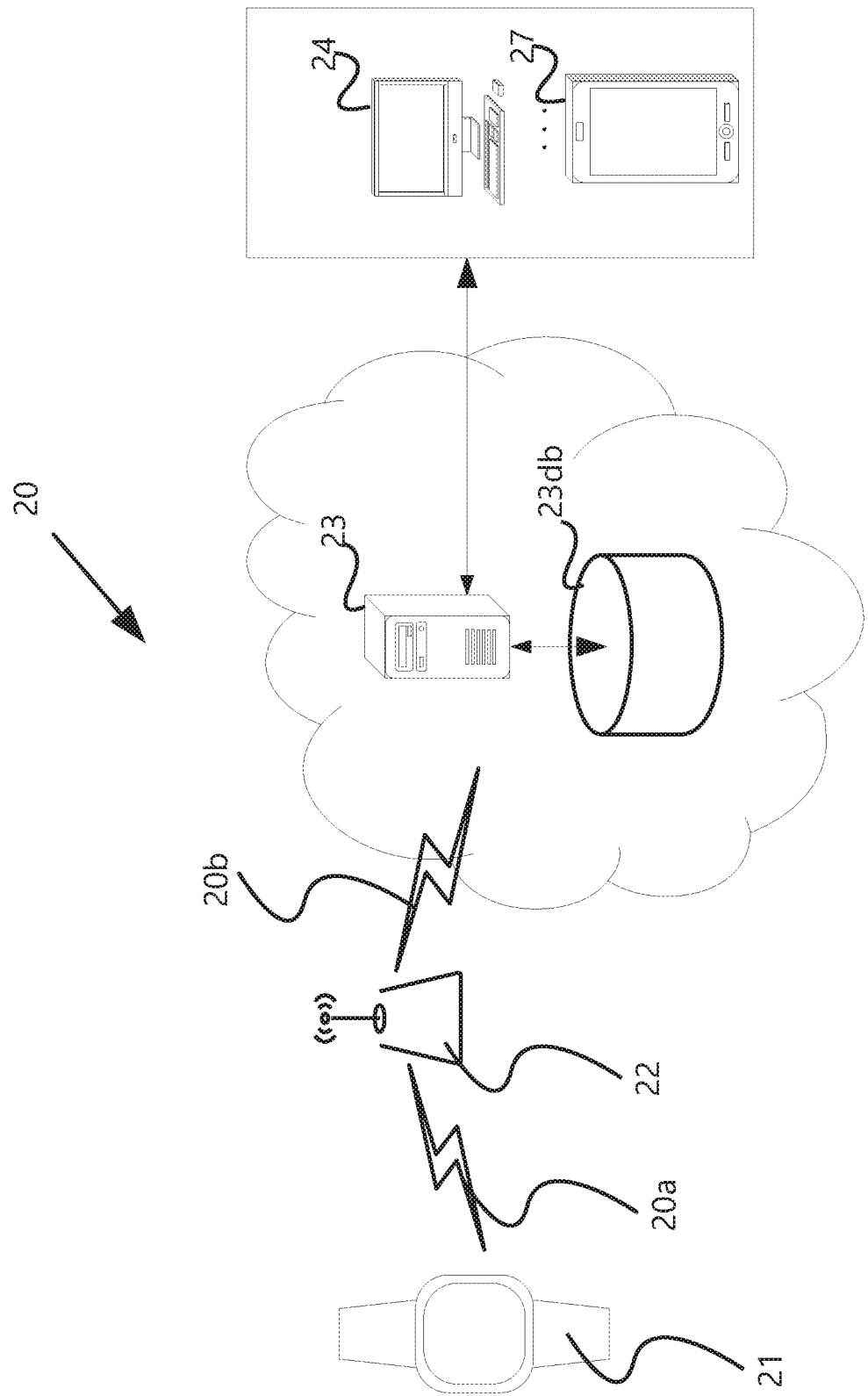
FIG. 4 is an exemplary illustration of a system in accordance with an embodiment.

FIG. 4 is an illustration of one system 20 of communicating a user's real-time physiological data with the web portal and providing a communication to the user. The system 20 includes a physiological monitoring device 21 that obtains real-time physiological data for a user and sends a transmission 20a to an antenna 222 of a communication network for communication 20b to a server 23 for a web portal 24. Then, a communication is sent to the user for display on a computing device, such as mobile device 27. In another example, the device 21 can send the transmission 20a to the user's mobile device 27, which then transmits the information to the server 23.

Figure 5:
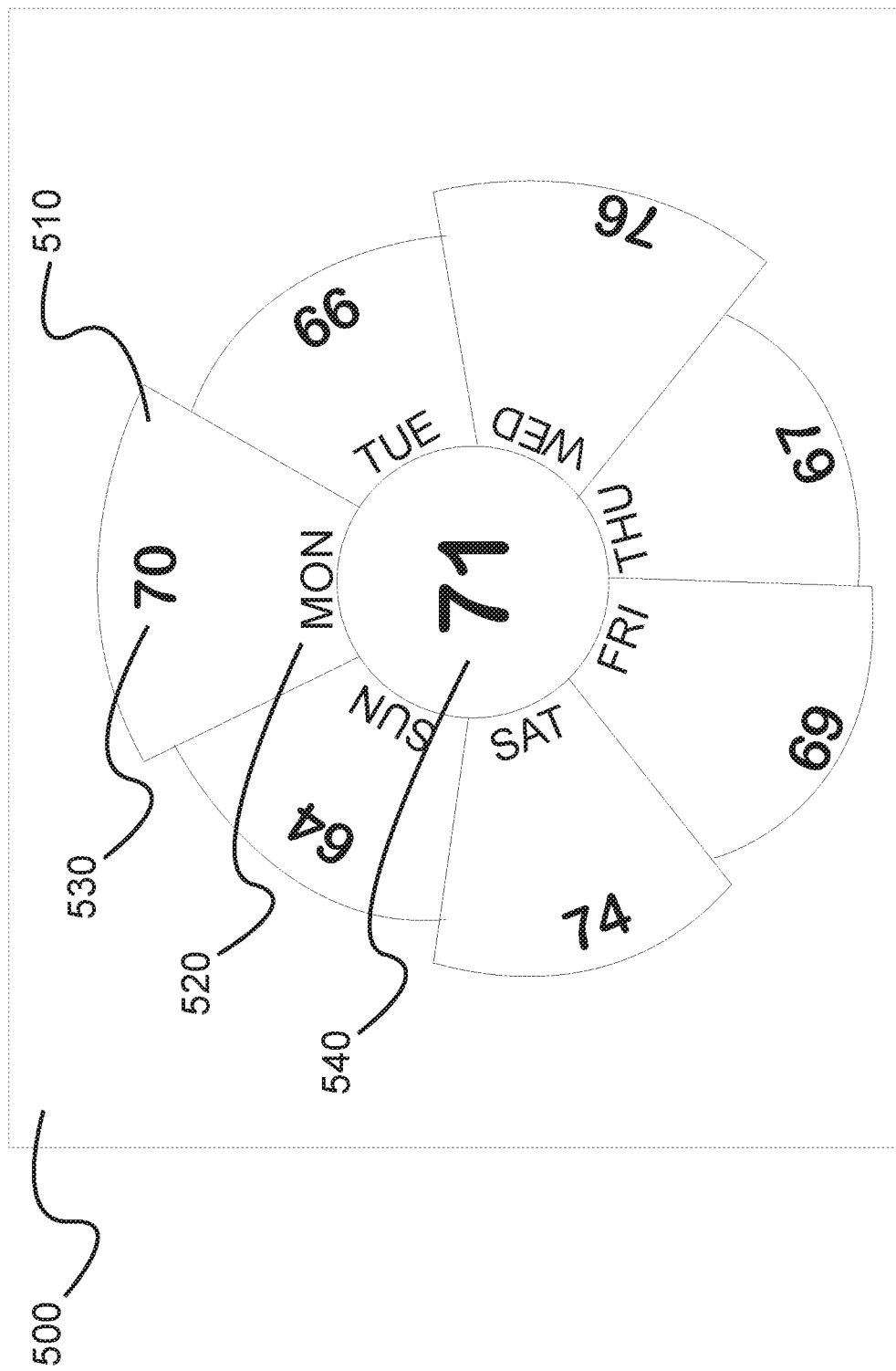
FIG. 5 is an illustration of an example graphical user interface in accordance with an embodiment.

FIG. 5 is an illustration of an example GUI 500 in accordance with various embodiments disclosed herein. The GUI 500 can be displayed on, for example, a wearable device of the user, a mobile device paired with the wearable device, or any other computing device capable of receiving physiological information obtained at the wearable device.

The GUI 500 includes an average HRV score 540 located in the center of the display. The average HRV score 540 can be an average based on any relevant period of time. In the example of FIG. 5, the average HRV score 540 is an average based on the previous week (for example, the previous Sunday-Saturday timespan. In other examples, the average HRV score 540 can be a moving average based on the previous seven days. The average HRV score 540 can be color-coded to provide the user with additional information. For example, it can be color-coded in accordance with the categories discussed above with respect to FIG. 3.

A user can select the circle associated with the average HRV score 540 for further information. For example, in response to the user selecting the average HRV score 540 on the GUI 500, the user can be presented with a detailed breakdown of the average HRV score 540. This can include, for example, the period of time for which the score is being calculated, the health category associated with the score and its implications for the users, as well as tips for improving the score going forward. Any other relevant information can be provided here as well.

The GUI 500 also includes graphics associated with each day of the week. Each of these graphics 510, or "slices" 510, can correspond to a particular day. For example, the slice 510 identified in FIG. 5 can correspond to Monday, and can include a day identifier 520 positioned near or within the slice 510. Each slice 510 can also include a daily HRV score 530. The daily HRV score 530 can be based on any relevant time period. For example, it can be based on a 24-hour period associated with the identified day. In another example where sampling happens only periodically, the daily HRV score 530 can be an average of HRV scores calculated based on the periodic sampling within a 24-hour period. In yet another example, the daily HRV score 530 can be a score reflecting a trailing average, such as a 2-, 4-, or 7-day trailing average.

A user can select a slice 510 to learn more information related to that slice 510. In response to the user selecting a slice 510, the GUI can present an additional display showing more detailed information associated with that slice 510. For example, the additional display can explain the time period for which the daily HRV score 530 is obtained, the health implications of the score, and suggestions for improving the score.

Although 7 slices 510 are shown in FIG. 5, any number can be displayed on the GUI 500. For example, the display can include 7 slices 510, with one for each day of the week and an additional one for a moving average based on a multiple-day span of time. Furthermore, although the scores displayed on the GUI 500 are described as various types of HRV scores, weighted HRV scores can be used instead of, or in addition to, these scores.

Figure 6:
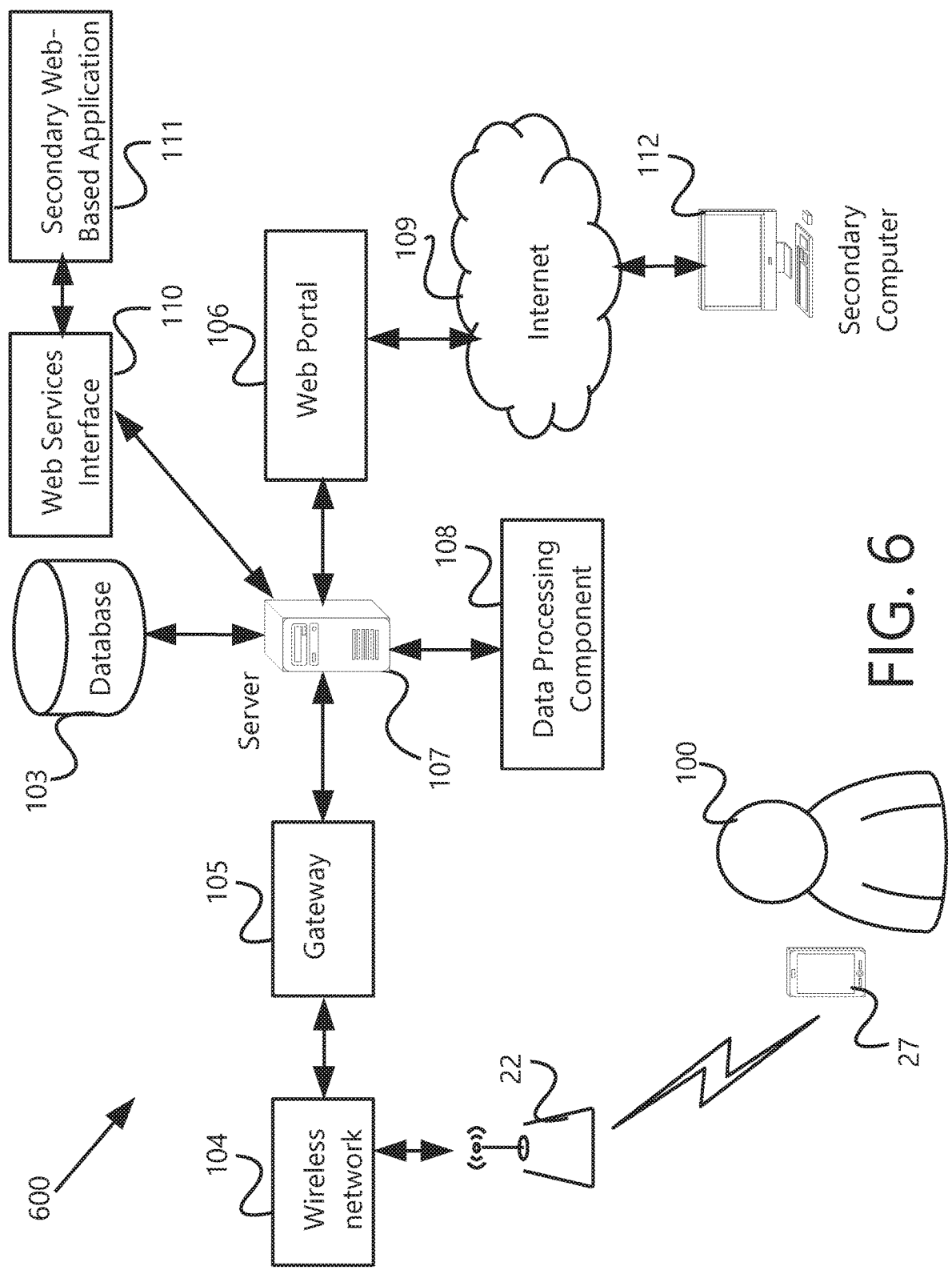
FIG. 6 is an exemplary illustration of a system in accordance with an embodiment.

A more detailed system of the present invention is shown in FIG. 6. The system 600 may operate the computing device 27 (such as a watch or phone) to transmit real-time physiological date from a user through a wireless network 104 to a web portal 106 hosted on an Internet-based server 107. A secondary computer 112 accesses the web portal 106 through the Internet 109. A wireless gateway 105 connects to the wireless network 104 and receives and delivers data from and to the device 27. The wireless gateway 105 additionally connects to the server 107 that includes a database 103 and a data-processing component 108 for, respectively, storing and analyzing the data.

The server 107, for example, may include multiple computers, software pieces, and other signal-processing and switching equipment, such as routers and digital signal processors. The wireless gateway 105 preferably connects to the wireless network 104 using a TCP/IP-based connection, or with a dedicated, digital leased line (e.g., a frame-relay circuit or a digital line running an X.25 or other protocols). The server 107 also hosts the web portal 106 using conventional computer hardware (e.g. computer servers for both a database and the web site) and software (e.g., web server and database software). Additionally, the server 107 includes a web services interface 110 that transmits data using an XML-based web services link to a secondary, web-based computer application 111. This application 111 is preferably a data-management system operating at a health clinic.

In one embodiment, the system 20 is a SUN MICROSYSTEM workstation such as the SPARCstation brand workstation manufactured by Sun Microsystems of Mountain View, Calif. Note that the following discussion of various embodiments discussed herein will refer specifically to a series of routines which are generated in a high-level programming language (e.g., the PERL, JAVA, PYTHON, SMALLTALK interpretive and scripting languages) which is interpreted and/or executed in system 20 at run-time.

These further are used in conjunction with the browser and server software available from NCSA, MOSAIC NETACAPE MICROSOFT and other SPYGLASS licenses including the specification of the appearance of displays in HTML. One skilled in the art appreciates that the following methods and apparatus may be implemented in special purpose hardware devices, such as discrete logic devices, large scale integrated circuits (LSI's), application-specific integrated circuits (ASIC's), or other specialized hardware. Other programming languages, C, BasicC, C++ and other Operating systems such as Unix, Posix, and variations of Linux platforms may be utilized.

Another embodiment Web Server platform comprises an IBM RISC System/6000 computer running the AIX (Advanced Interactive Executive) Operating System and a Web server program, such as Netscape Enterprise Server Version 2.0, that supports interface extensions. The platform also includes a graphical user interface (GUI) for management and administration. The various models of the RISC-based computers are described in many publications of the IBM Corporation, for example, RISC System 6000, 7013 and 7016 POWERstation and POWERserver While the above platform is useful, any other suitable hardware/operating system/Web server combinations may be used. Accordingly, the web server description here has equal application to apparatus having similar components and functions.

Figure 7:
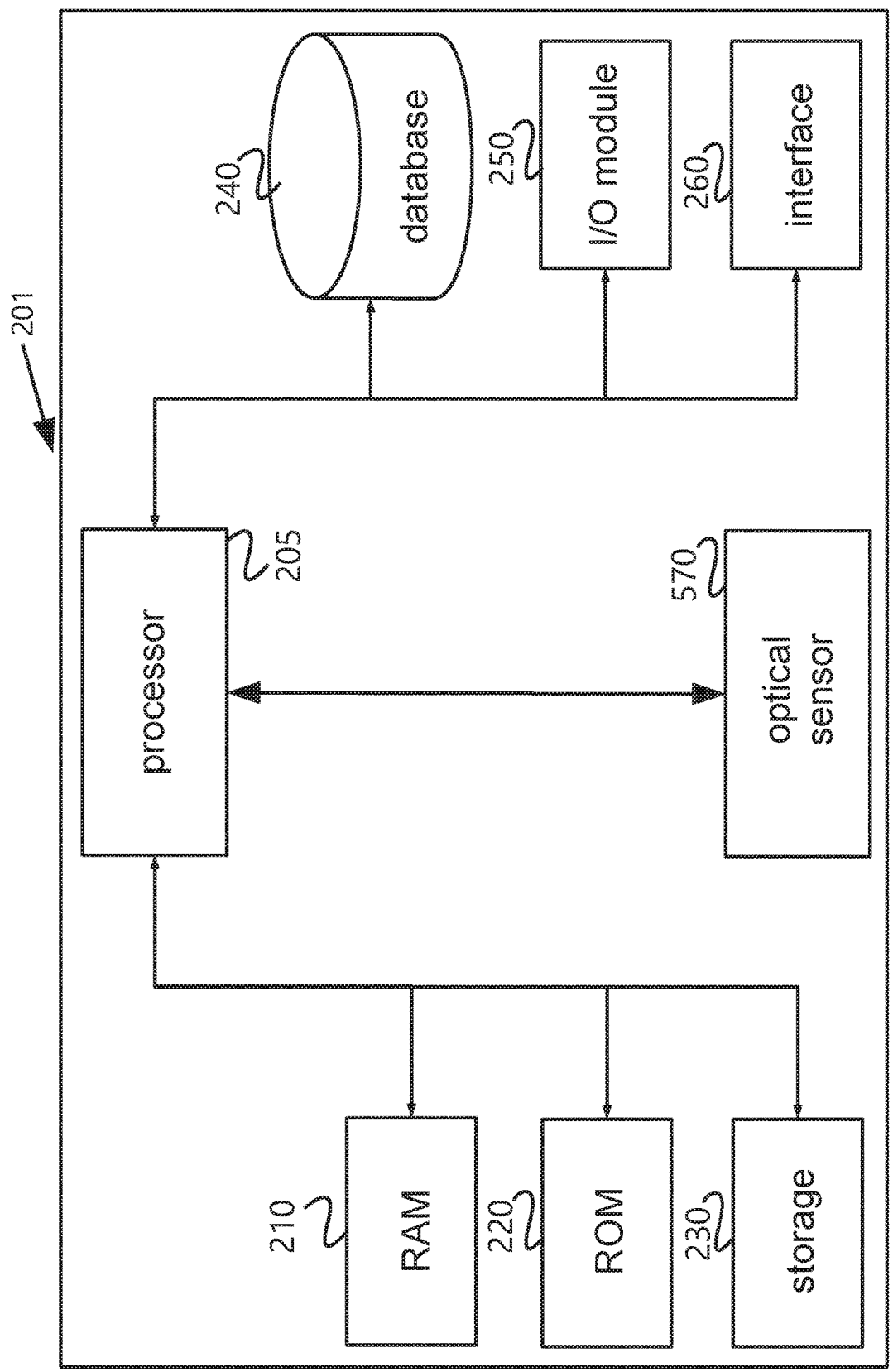
FIG. 7 is an exemplary illustration of system components in accordance with an embodiment.

FIG. 7 depicts an exemplary processor-based computing system 201 representative of the type of computing system that may be present in or used within the computing device 27 or serve 107 in an embodiment. The computing system 201 is exemplary only and does not exclude the possibility of another processor- or controller-based system being used in or with one of the aforementioned components.

In one aspect, system 201 may include one or more hardware and/or software components configured to execute software programs, such as software for storing, processing, and analyzing data. For example, system 201 may include one or more hardware components such as, for example, processor 205, a random access memory (RAM) module 210, a read-only memory (ROM) module 220, a storage system 230, a database 240, one or more input/output (I/O) modules 250, and an interface module 260. Alternatively and/or additionally, system 201 may include one or more software components such as, for example, a non-transitory computer-readable medium including computer-executable instructions for performing methods consistent with certain disclosed embodiments. It is contemplated that one or more of the hardware components listed above may be implemented using software. For example, storage 230 may act as digital memory that includes a software partition associated with one or more other hardware components of system 201. System 201 may include additional, fewer, and/or different components than those listed above. It is understood that the components listed above are exemplary only and not intended to be limiting.

Processor 205 may include one or more processors, each configured to execute instructions and process data to perform one or more functions associated with system 201. The term "processor," as generally used herein, refers to any logic processing unit, such as one or more central processing units (CPUs), digital signal processors (DSPs), application specific integrated circuits (ASICs), field programmable gate arrays (FPGAs), and similar devices, such as a controller. As illustrated in FIG. 2A, processor 205 may be communicatively coupled to RAM 210, ROM 220, storage 230, database 240, I/O module 250, and interface module 260. Processor 205 may be configured to execute sequences of computer program instructions to perform various processes, which will be described in detail below. The computer program instructions may be loaded into RAM for execution by processor 205.

RAM 210 and ROM 220 may each include one or more devices for storing information associated with an operation of system 201 and/or processor 205. For example, ROM 220 may include a memory device configured to access and store information associated with system 201, including information for identifying, initializing, and monitoring the operation of one or more components and subsystems of system 201. RAM 210 may include a memory device for storing data associated with one or more operations of processor 205. For example, ROM 220 may load instructions into RAM 210 for execution by processor 205.

Storage 230 may include any type of storage device configured to store information that processor 205 may need to perform processes consistent with the disclosed embodiments.

Database 240 may include one or more software and/or hardware components that cooperate to store, organize, sort, filter, and/or arrange data used by system 201 and/or processor 205. For example, database 240 may include information to that tracks physiological parameters, activity types and levels, and HRV for users based on embodiments herein. Alternatively, database 240 may store additional and/or different information. Database 240 may also contain a plurality of databases that are communicatively coupled to one another and/or processor 205, of may connect to further database over the network.

I/O module 250 may include one or more components configured to communicate information with a user associated with system 201. For example, I/O module 250 may include a console with an integrated keyboard and mouse to allow a user to input parameters associated with system 201, such as the identification of the user to independently track different users of the computing device (e.g., a watch shared by different users). I/O module 250 may also include a display including a graphical user interface (GUI) for outputting information on a monitor. I/O module 250 may also include peripheral devices such as, for example, a printer for printing information associated with system 201, a user-accessible disk drive (e.g., a USB port, a floppy, CD-ROM, or DVD-ROM drive, etc.) to allow a user to input data stored on a portable media device, a microphone, a speaker system, or any other suitable type of interface device.

Interface 260 may include one or more components configured to transmit and receive data via a communication network, such as the Internet, a local area network, a workstation peer-to-peer network, a direct link network, a wireless network, or any other suitable communication platform, such as Bluetooth. For example, interface 260 may include one or more modulators, demodulators, multiplexers, demultiplexers, network communication devices, wireless devices, antennas, modems, and any other type of device configured to enable data communication via a communication network.

Optical sensor 570 may allow the system 201 to determine if a user is inside or outside, or in a lighted versus darkened room. This may allow for further insights into the user's activity in conjunction with other sensors that detect motion or physiological attributes.

In one embodiment, the system may continuous test physiological parameters of a user, including periodic recording of heart rate variability, to assess stress level and physical fitness of users. The assessment may be carried out automatically during user's usual daily physical activity.

Figure 8:
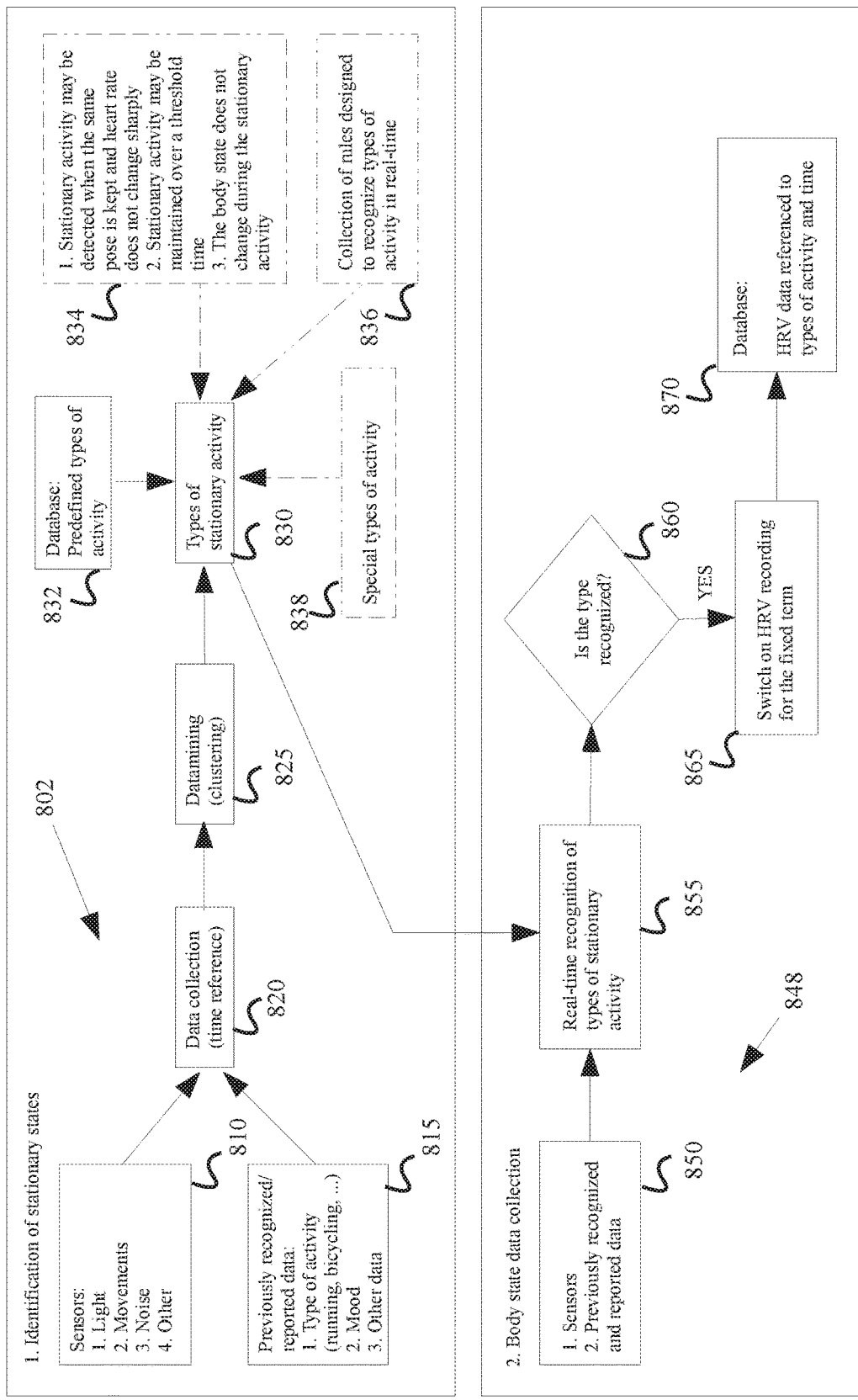
FIG. 8 is an exemplary flow chart in accordance with an embodiment.
Figure 9:
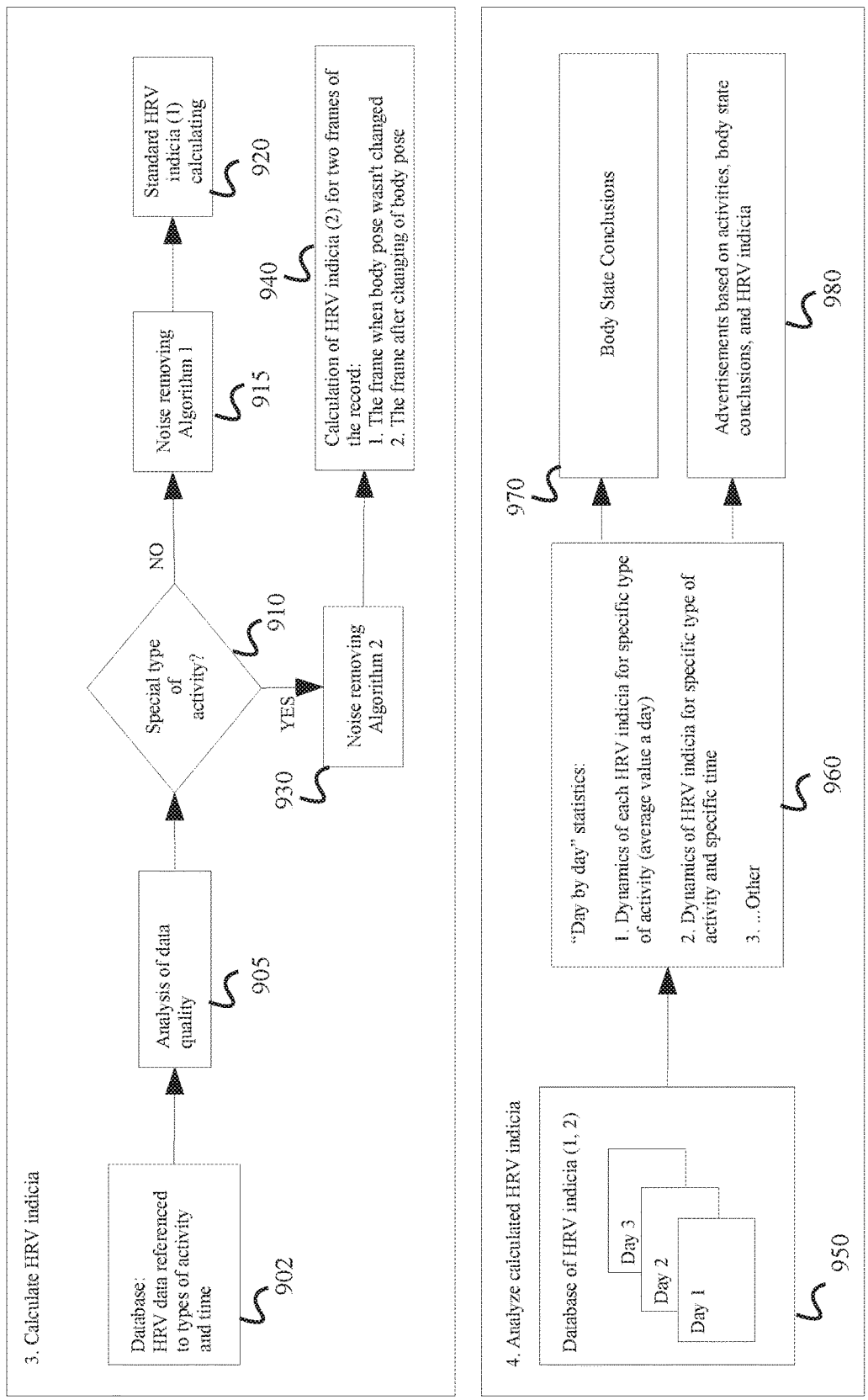
FIG. 9 is an exemplary flow chart in accordance with an embodiment.

FIGS. 8 and 9 include exemplary steps for continuously testing activity data and the physiological parameters of a user. FIG. 8 includes example steps for identifying stationary states of a user and for collecting data regarding body states of a user. At 802, exemplary steps related to detecting a stationary state are shown.

At step 810, various sensors in a computing device, such as a wrist-worn watch or bracelet, may detect light, movement, noise, or other environmental characteristics that may be used as sensed activity data. Sensors such as an optical sensor, piezoelectric sensor, accelerometer, and/or microphone, may make these detections. Other sensed characteristics may include temperature or temperature change. This may indicate that a user has, for example, transitioned from outdoors to indoors or vice versa. Another characteristic may be light frequency, which may inform the type of environment the user is in. For example, the light frequencies of fluorescent lighting differ from those of sunlight. Other data, such as the sound of typing, the sound of talking, or oxygen or blood flow levels consistent with various types of activity may be recorded via the various sensors.

At step 815, other activity data representative of user activities or other attributes may be input by the user and/or retrieved by a server. For example, through inputting activity data, the user may indicate an activity, such as running, cycling, swimming, hiking, or weight lifting is taking place by selecting an activity on their computing device. Other attributes, such as mood, may be input by the user, such as with respect to a social media profile. Age may also be input by the user, for use in adjusting HRV insights made by the system, since age and HRV are correlated.

The user may also indicate a location where they are present that provides insight into their activities, such as a restaurant location, a gym location, or a sporting event location. In one embodiment, the computing device uses GPS to collect this information. In still another embodiment, data regarding the apparel (e.g., clothes or shoes) of the user may be collected through user input or though wireless connection between the apparel and the computing device. The apparel worn may indicate the user's activity based on differences in purpose of work apparel, sleep apparel, and exercise apparel.

At step 820, the data from steps 810 and 815 may be collected on the computing device and/or a server that communicates with the computing device. This may include storing the data in a database with respect to a particular user identifier.

At step 825, the server may make determinations regarding the user's activity by analyzing patterns in the collected data, such as through cluster analysis-type data mining. Other techniques for machine learning, pattern recognition, and bioinformatics may be incorporated in addition or in the alternative. This may help remove or diminish the weight of outlier data and noise from the analysis. The cluster model may include algorithms based on both the sensor inputs of step 810 and the user inputs of step 815.

The analysis may include a comparison against predefined types of activity that are stored in a database 832. The database 832 may include predefined rules that allow the system to identify and recognize different activity types. Different activities may include sitting, television watching, driving, jogging, sleeping, eating, working at a desk, gardening, lifting weights, and more.

In one embodiment, the database may be continuously updated by the system to learn new patterns indicative of particular states based on both the step 810 and 815 data. The rules may be in flux based on user-verified activities.

For example, at step 830, the system may collect new rules based on the determinations at step 825 and/or adjust existing predefined rules in database 832 based on a user's particular habits. For example, a particular user may have a proclivity for a certain activity type during a particular time period, so the rules may be adjusted specifically for that user to bias towards the activity type during the detected time period.

From those data-defined activities, particular stationary activity may be determined at step 830 in real time. The system may utilize rules at 836 to compare real-time data against historical patterns in the database at step 832. Various patterns and indicia may be analyzed to determine the stationary activity. For example, as shown in step 834, stationary activity may be indicated when the same pose is kept and heart rate does not change abruptly. A consistent heart rate and body location tend to indicate stationary activity.

This may be analyzed to determine the user is stationary based on one or more time thresholds. For example, the heart rate and movement of a user may be tracked over 60 seconds, 128 seconds, and 256 seconds in one embodiment. The different time thresholds may allow for determining different types of stationary activity if the body state does not change over those time thresholds. In another embodiment, recording of user heart rate and movement continues during an activity even after that specific activity has been recognized. This recorded data may be utilized to further develop the pattern recognition involved in identifying the activity again in the future.

Other special types of activity and stationary activities may be determined at step 838. For example, a sharp change in body pose, such as from laying down to standing up in a short time (e.g., less than five minutes) may be detected.

Additional exemplary body state data collection steps are shown at 848. At step 850, sensors and previously recognized and/or reported data may be utilized by the system in analyzing body state.

At step 855, the system may recognize types of activity, including stationary activity, in real time. If a particular state is recognized at step 860, then HRV recording may be switched on at step 865. Other types of data may also be collected as step 865, such as blood pressure. Based on the recorded HRV and/or other collected data, a particular state (such as stress level) may be verified and/or a determination may be made regarding when the state is ending. Additionally, HRV data collection may allow for analysis of quality of rest and other characteristics within a stationary state.

Continuing at FIG. 9, exemplary steps for calculating HRV indices are illustrated at 900. At step 902, the database is queried to obtain the recorded HRV data and reference the data to activity types and timing thresholds. The data may be analyzed at step 905 to determine if a special type of activity is present, such as a user sitting up or rolling over at 910.

If a special type of activity is not detected, then the system may apply a first noise removing algorithm at 915. Then at step 920, the system may calculate HRV indicia (also referred to herein as HRV indexes).

Alternatively, if a special type of activity is detected, the system may perform a different noise removing algorithm at step 930 and then, at step 940, calculate HRV indicia separately according to when the body position or pose was unchanged and after the body position or pose changed. The noise removing algorithm may be specific to the detected type of activity and/or analog sensor relied on because different activities may tend to introduce different types and/or levels of noise. Thus, recognizing an activity also may cause the system to apply a more suitable noise algorithm, meaning that the number of noise algorithms may equal the number of activities in one embodiment.

These calculated HRV indicia are then further analyzed, such as through the exemplary steps shown at 945. For example, at step 950 HRV indicia for multiple days may be analyzed to generate insights for the user. As shown at 960, day by day statistics may include values representative of how much the user performs each specific activity type per day. The user may be able to use an app, web interface, or display on a watch to see specific activity statistics for each day in one embodiment. In another embodiment, the statistics may be presented as bar charts, and bars may represent activity levels for each activity. Bar graphs for multiple days may be overlaid on top of one another to easily visualize changes per day. The activity levels may be given scores within the range of 0 to 100 to give a user a numeric reference to strive towards.

In another embodiment, the user may be able to select a particular activity and day and see specific details about that activity, such as heart rate, duration, location, and others.

At step 970, the system may also present conclusions to the user regarding the user's body state. For example, the system may determine that the user's body state is good, strained, or poor in one embodiment. These insights may allow the user to better tailor activity regimens (e.g., exercise) such that their body state is not poor or strained.

In another embodiment, the conclusion indicates that the user has one of a variety of physiological characteristics, including a high or low blood pressure, high or low stress level, underweight or overweight, rapid heartbeat or arrhythmia, possibility of disease, or improving health compared to other similar users.

At step 980, the system may present advertisements to the user in conjunction with the statistics and/or conclusions. For example, if the user is having trouble sleeping, as determined by their sleep state being below an activity threshold, fluctuations of HRV during sleep, and/or sudden movements during sleep, an advertisement for sleep assistance product may be presented. Similarly, if the daily levels for exercising are low, the user may be presented with gym advertisements. If the activity level for running begins to increase but running causes a HRV to change more than a threshold amount over a time frame, advertisements directed to new runners may be displayed.

Other embodiments of the aforementioned systems and methods will be apparent to those skilled in the art from consideration of the specification and practice of this disclosure. It is intended that the specification and the aforementioned examples and embodiments be considered as illustrative only, with the true scope and spirit of the disclosure being indicated by the following claims.

What is claimed is:

1. A system for providing user insights based on heart rate variability (HRV), comprising:
a wearable device that obtains real-time physiological data from a user, obtains activity data from a user, and transmits the real-time physiological data and activity data; and
a processor configured to:
receive the physiological data and the activity data,
wherein the physiological data is used to calculate the HRV,
wherein the activity data describes at least two of a physical state of the user, the wearable device, or an environment of the user, and
wherein the activity data comprises at least three of the accelerometer-based movements of the user, illumination information, illumination change information, atmospheric pressure information, activity type, apparel worn by the user, running speed and distance information, step information, temperature information, temperature change information, light frequency, sound information, or location information;
identify, using the activity data, a stationary state of the user; and
in response to identifying the stationary state:
determine, based on correlating the physiological data and the activity data, whether the user's autonomic nervous system is in a predominantly parasympathetic state; and
in response to determining that the user's autonomic nervous system is in a parasympathetic state, perform an action.

2. The system of claim 1, wherein determining whether the user's autonomic nervous system is in a predominantly parasympathetic state comprises calculating a heart rate variability score and comparing the score to a threshold value.

3. The system of claim 1, wherein determining whether the user's autonomic nervous system is in a predominantly parasympathetic state comprises calculating a heart rate variability score, weighting the score based on information associated with the user, and comparing the weighted score to a threshold value.

4. The system of claim 3, wherein the information associated with the user includes at least one of the user's age, sex, physical fitness level, and fitness history.

5. The system of claim 1, wherein performing an action comprises providing an alert to the user indicating that the user is under stress.

6. The system of claim 1, wherein performing an action comprises recommending an activity for the user to perform.

7. The system of claim 1, wherein performing an action comprises dimming or turning off a light.

8. The system of claim 1, wherein performing an action comprises playing music or adjusting the volume of music.

9. A method for providing user insights based on heart rate variability, comprising:
receiving physiological data and activity data obtained in real time from a user;
determining, based on the physiological data and the activity data, whether the user's autonomic nervous system is in a predominantly parasympathetic state by steps comprising;
identifying, using the activity data, a stationary state of the user using a body state of the user, wherein the stationary state is identified using criteria including identifying the stationary state when a same body position or pose of the user is kept and a heart rate does not change abruptly during a time threshold; and
in response to not identifying an activity associated with the stationary state, calculating a first heart rate variation indicium and a second heart rate variation indicium separately according to when the same body position or pose was unchanged and after the body position or pose changed; and
in response to determining that the user's autonomic nervous system is in a parasympathetic state, performing an action.

10. The method of claim 9, wherein determining whether the user's autonomic nervous system is in a predominantly parasympathetic state comprises calculating a heart rate variability score and comparing the score to a threshold value.

11. The method of claim 9, wherein determining whether the user's autonomic nervous system is in a predominantly parasympathetic state comprises calculating a heart rate variability score, weighting the score based on information associated with the user, and comparing the weighted score to a threshold value.

12. The method of claim 11, wherein the information associated with the user includes at least one of the user's age, sex, physical fitness level, and fitness history.

13. The method of claim 9, wherein performing an action comprises providing an alert to the user indicating that the user is under stress.

14. The method of claim 9, wherein performing an action comprises recommending an activity for the user to perform.

15. The method of claim 9, wherein performing an action comprises a first action of dimming or turning off a light or a second action of playing music or adjusting the volume of the music.

16. The method of claim 9, further comprising:
   calculating a plurality of heart rate variability scores using at least the physiological data for a respective plurality of time periods; and
   displaying, on a device of the user, each of the plurality of the heart rate variability scores in a respective slice of a doughnut-shaped graph,
      wherein the respective slices have equal widths,
      wherein the respective slices have respective heights indicative of respective magnitudes of the heart rate variability scores, and
      wherein an average of the plurality of the heart rate variability scores is displayed at a center of the doughnut-shaped graph.

17. A non-transitory, computer-readable medium containing instructions that, when executed by the processor of a computing device, cause the processor to carry out stages for providing user insights based on heart rate variability, the stages comprising:
   receiving physiological data and activity data obtained in real time from a user,
      wherein the physiological data is used to calculate the HRV,
      wherein the activity data describes at least two of a physical state of the user, the wearable device, or an environment of the user, and
      wherein the activity data comprises at least three of the accelerometer-based movements of the user, illumination information, illumination change information, atmospheric pressure information, activity type, apparel worn by the user, running speed and distance information, step information, temperature information, temperature change information, light frequency, sound information, or location information;
   identify, using the activity data, a stationary state of the user; and
   in response to identifying the stationary state:
      determine, based on correlating the physiological data and the activity data, whether the user's autonomic nervous system is in a predominantly parasympathetic state; and
      in response to determining that the user's autonomic nervous system is in a parasympathetic state, perform an action.

18. The non-transitory, computer-readable medium of claim 17, further comprising:
   determining, based on at least the physiological data, whether the user's autonomic nervous system is in a predominantly parasympathetic state,
      wherein determining whether the user's autonomic nervous system is in a predominantly parasympathetic state comprises calculating a heart rate variability score and comparing the score to a threshold value; and
   in response to determining that the user's autonomic system is in a parasympathetic state and to identifying that the user is driving:
      identifying based on the location of the user a proximal location to stop; and
      informing the user to stop at the location to perform an activity, wherein the activity is at least one of resting or exercising.

19. The non-transitory, computer-readable medium of claim 17, wherein determining whether the user's autonomic nervous system is in a predominantly parasympathetic state comprises calculating a heart rate variability score, weighting the score based on information associated with the user, and comparing the weighted score to a threshold value.

20. The non-transitory, computer-readable medium of claim 19, wherein the information associated with the user includes at least one of the user's age, sex, physical fitness level, and fitness history.

* * * * *